United States Patent [19]

Muetterties

[11] 4,223,695
[45] Sep. 23, 1980

[54] NOVEL VALVE EMPLOYING HYDROPHOBIC AND HYDROPHILIC MEMBRANES

[75] Inventor: Andrew J. Muetterties, Gages Lake, Ill.

[73] Assignee: Abbott Laboratories, North Chicago, Ill.

[21] Appl. No.: 16,228

[22] Filed: Feb. 28, 1979

[51] Int. Cl.² .................... F16T 1/04; A61M 5/00
[52] U.S. Cl. ................ 137/173; 137/199; 137/183; 55/159; 128/214 R; 128/214 G
[58] Field of Search .......... 128/214 R, 214 C, 214 L, 128/214 G, 227; 210/DIG. 23, 484; 137/113, 183, 198, 199; 55/159

[56] References Cited

U.S. PATENT DOCUMENTS

| | | | |
|---|---|---|---|
| 3,886,937 | 6/1975 | Bobo et al. | 128/214 G |
| 3,993,066 | 11/1976 | Virag | 128/214 C |
| 4,031,891 | 6/1977 | Jess | 128/214 R |
| 4,116,646 | 9/1978 | Edwards | 55/159 |
| 4,136,693 | 1/1979 | Dyke | 128/214 C |

*Primary Examiner*—Dalton L. Truluck
*Attorney, Agent, or Firm*—Robert L. Niblack; Aaron L. Hardt

[57] ABSTRACT

A novel valve employing hydrophobic and hydrophilic membranes and providing a combined air barrier and liquid sequencing valve. The novel valve is useful in gravitational flow systems and equipment sets for the sequential administration of medical liquids, wherein a primary liquid can be administered at a flow rate independent of the flow rate of a secondary liquid, and includes barriers substantially impervious to air to prevent the inadvertent administration of air when the liquids are depleted.

6 Claims, 5 Drawing Figures

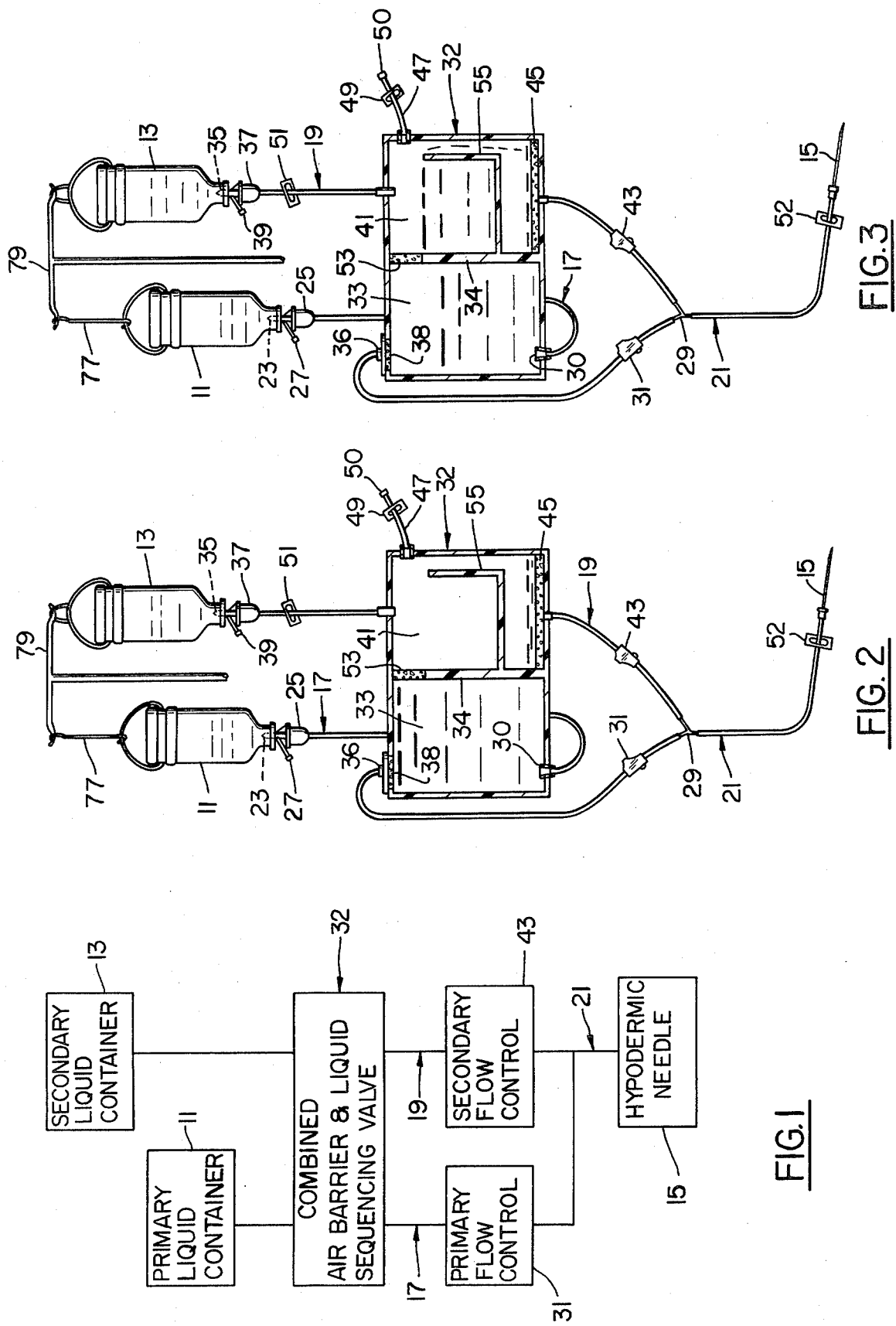

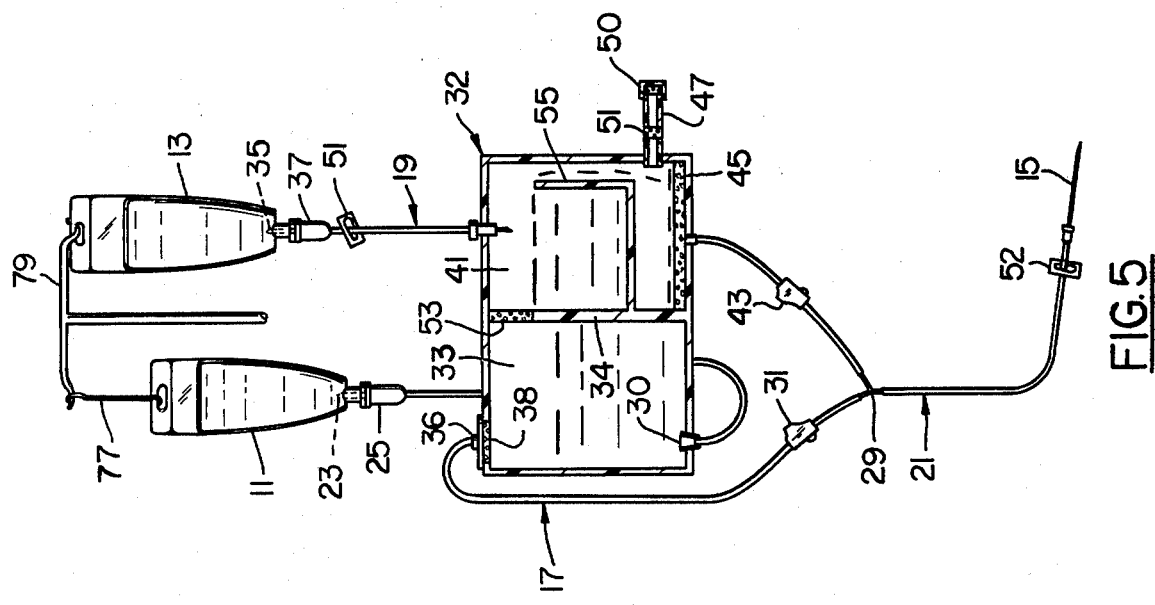
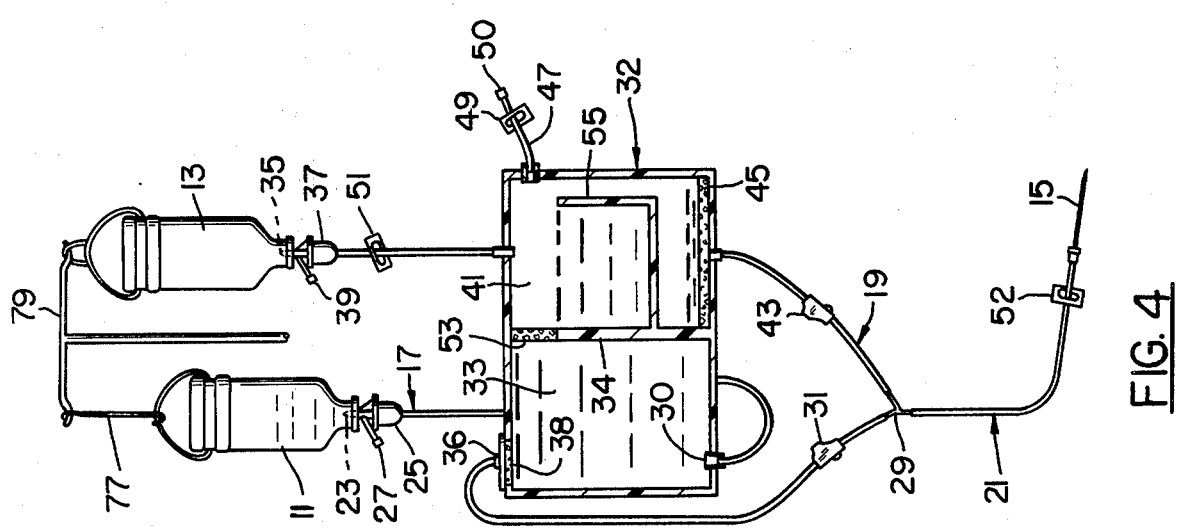

NOVEL VALVE EMPLOYING HYDROPHOBIC AND HYDROPHILIC MEMBRANES

BACKGROUND OF THE INVENTION

The present invention relates to systems and equipment sets for the administration of medical liquids to a patient, and more particularly, to systems and equipment sets for the sequential administration of a plurality of medical liquids employing a novel hydrophobic and hydrophilic membrane valve providing a combined air barrier and liquid sequencing valve therefor.

The parenteral administration of medical liquids to patients is a long established practice. Liquids including amino acids, blood, dextrose, electrolytes, and saline are commonly administered to patients over prolonged periods of time. Generally, these liquids are administered from a glass bottle or plastic bag suspended above the patient and containing 250–2,000 ml. of the liquid. Such prolonged infusions commonly are administered at a flow rate of 10–150 ml./hr.

Frequently, the patient must receive an additive or secondary liquid while the prolonged infusion is being administered. Preferably, this secondary liquid should be administered through the same hypodermic needle to avoid unnecessary pain and trauma to the patient of additional venipunctures. To avoid dilution and incompatability problems, it is also preferable that the flow of the primary liquid employed in the prolonged infusion be temporarily interrupted, the secondary liquid administered and the flow of the primary liquid resumed. Generally, the secondary liquid will be administered at a flow rate of 50–250 ml./hr.

Abbott Laboratories, North Chicago, Ill. manufactures a y-type set for the sequential administration of primary and secondary liquids. These VENOSET piggyback sets allow the prolonged infusion of a primary liquid to be temporarily halted by means of a backcheck valve in the primary liquid flow path to administer a secondary liquid without the need for a new venipuncture. Then, when the secondary liquid has been depleted, the backcheck valve automatically opens to resume flow of the primary liquid. An important characteristic of this system is that the secondary liquid container must be suspended at a higher height than the primary liquid container to establish the liquid pressure differential that closes the backcheck valve in the primary liquid flow path.

A similar system is disclosed in U.S. Pat. No. 3,886,937 granted June 3, 1975 to D. Bobo, et al., assigned to American Hospital Supply Corp., and entitled "Medical Administration Set for Dispensing Plural Medical Liquids". Another similar system is disclosed in U.S. Pat. No. 4,105,029 granted Aug. 8, 1978 to R. Virag, assigned to Baxter Travenol and entitled "Intravenous Solution Set Having An Air Access Site and Constricted Inner Diameter Portion".

An inherent disadvantage of the above-mentioned prior art medical liquid administration systems is that they each resume the flow of primary liquid at the rate the secondary liquid had been flowing. Because the preferred flow rate of the secondary liquid is generally greater than the preferred flow rate of the primary liquid, when the primary liquid resumes flow at that rate, the patient can be administered an excessive amount of primary liquid, unless the flow rate of the primary liquid is adjusted to the preferred primary liquid flow rate soon after the flow of primary liquid resumes.

A remedy to the above-described disadvantage would appear to be provided by simply incorporating flow control devices into both the primary and secondary liquid flow paths. However, while this remedy does provide dual flow rates for the primary and secondary liquids, it is unacceptable. That is, because the common tube of the y-set must be able to accommodate both flow rates, when the primary liquid is flowing at a slower rate than the secondary liquid was, there will be an unfilled volume or void in the common tube. To fill that void, air will be drawn into the common tube from the depleted secondary container. That air will then be driven into the patient by the weight of the primary liquid, thereby causing a serious embolism and perhaps, the patient's death.

Accordingly, it will be apparent that a device for sequencing the flow of a plurality of liquids and preventing the flow of air therethrough when the liquids have been depleted would be advantageous to the medical profession.

SUMMARY OF THE INVENTION

The primary object of the present invention, therefore, is to provide a combined air barrier and liquid sequencing valve for the sequential administration of medical liquids at dual flow rates that will not draw air from the liquid containers when the liquids have been depleted.

In accordance with this and other objects, there is provided by the present invention a gravitational flow system for the sequential administration of medical liquids to a patient including a primary liquid container, a primary tube, a secondary liquid container, a secondary tube, and a common tube all connected in fluid communication to form a primary liquid flow path and a secondary liquid flow path. The primary liquid flow path includes the primary and common tube, while the secondary liquid flow path includes the secondary and common tubes.

To establish the dual flow rates of the primary and secondary liquids, a secondary flow control means in the secondary liquid flow path for adjusting the flow rate of the secondary liquid and a primary flow control means on the primary tube for adjusting the flow rate of the primary liquid to a rate independent of the flow rate of the secondary liquid are provided.

The primary tube includes a valve which allows primary liquid to flow from the primary container whenever the height of primary liquid is greater than or equal to the height of the secondary liquid in the system. The valve prevents primary liquid from flowing out of the primary container whenever the height of the primary liquid is less than the height of the secondary liquid in the system. The valve is also impermeable by air when the primary liquid is depleted from the primary container. An air barrier in the secondary liquid flow path that is substantially impervious to air is provided to insure that no air is drawn from the secondary container when the secondary liquid is depleted. The secondary tube air barrier and primary tube valve are housed in a combined air barrier and liquid sequencing valve.

BRIEF DESCRIPTION OF THE DRAWING

Other objects and attendant advantages will become obvious to those skilled in the art by reading the following detailed description in connection with the accompanying drawing, wherein like reference characters designate like or corresponding parts throughout the several figures thereof and wherein:

FIG. 1 is a schematic block diagram of the efficacious system for the sequential administration of medical liquids at dual flow rates contemplated by this invention, and FIGS. 2-5 are front elevational views partially in cross-section illustrating the operation of a medical liquid administration equipment set embodying the system of FIG. 1 and employing the novel combined air barrier and liquid sequencing valve of this invention.

DETAILED DESCRIPTION OF THE INVENTION

Referring to the drawing, there is shown in FIG. 1, a schematic block diagram of the basic elements of the gravitational flow system for the sequential administration of medical liquids at dual flow rates contemplated by this invention.

The diagram depicts a primary liquid container 11 that contains a primary medical liquid to be administered to a patient for a prolonged period of time. The diagram also depicts a secondary liquid container 13 that contains a secondary medical liquid to be administered to the patient for a relatively short period of time, during which time the administration of the primary liquid will be temporarily interrupted. As shown in the sets of FIGS. 2 and 5, containers 11 and 13 can be glass bottles, plastic flexible bags, or any other suitable container.

Primary container 11 and secondary container 13 are connected in fluid communication to a conventional hypodermic needle 15 through a primary tube 17, a secondary tube 19, and a common tube 21. Thus, the primary liquid flow path from primary container 11 to needle 15 comprises primary tube 17 and common tube 21. Likewise, the secondary liquid flow path from secondary container 13 to needle 15 comprises secondary tube 19 and common tube 21.

The distal end of primary tube 17 is in fluid communication with primary container 11, preferably by means of a piercing pin 23 inserted into a puncturable closure of container 11. Piercing pin 23 can have an integral drip chamber 25, and when container 11 is a glass bottle, as shown in the set of FIG. 2, an integral, filtered air vent 27. Such piercing pins, drip chambers and air vents are well known in the medical practice and need not be more fully explained here.

The proximal end of primary tube 17 is joined in fluid communication to the distal end of common tube 21, preferably by a y-tube 29, it being understood that the primary, secondary and common legs of y-tube 29 constitute a portion of the primary, secondary and common tubes 17, 19 and 21, respectively. Primary tube 17 has a primary flow control 31 at any convenient location intermediate its ends for independently adjusting the rate of flow of the primary liquid through the primary liquid flow path. Preferably, as shown in FIGS. 2-5, primary flow control 31 can be a roller clamp. However, it can be any other adjustable device that will reliably maintain a desired primary liquid flow rate.

The distal end of secondary tube 19 is in fluid communication with secondary container 13, preferably, by means of a piercing pin 35 inserted into a puncturable closure of container 13. Piercing pin 35 can have an integral drip chamber 37, and when container 13 is a glass bottle, as shown in FIG. 2, an integral, filtered air vent 39. The proximal end of secondary tube 19 is joined in fluid communication to the distal end of common tube 21, preferably, by a y-tube 29.

A secondary flow control 43 is disposed at any convenient location in the secondary liquid flow path. Preferably, as shown in FIGS. 2-5, secondary flow control 43 can be a roller clamp. However, it can be any other adjustable device that can reliably maintain a desired secondary fluid flow rate.

A combined air barrier and liquid sequencing valve having a housing 32 is shown in FIG. 1. Housing 32 has first and second chambers 33, 41, as shown in FIGS. 2-5, that are formed by a vertical wall 34. First and second chambers 33, 41 each have inlet and outlet ports thereto through housing 32 that are respectively connected in fluid communication to the other portions of the primary or secondary tubes 17, 19. Primary tube 17 thus includes first chamber 33 of housing 32, while secondary tube 19 includes second chamber 41.

First chamber 33 has valve means associated with its ports that allow primary liquid to flow from primary container 11 whenever the height of the primary liquid is greater than or equal to the height of the secondary liquid in the system of FIG. 1. Further, the valve means associated with first chamber 33 prevents the flow of primary liquid from primary container 11 whenever the height of the primary liquid is less than the height of the secondary liquid in the system.

As shown in FIG. 2 and more fully explained in the following explanation of the operation of the sets of this invention, the valve means associated with first chamber 33 is a hydrophilic membrane 38 which covers outlet port 36 at the top of first chamber 33. Preferably, inlet port 30 is located at the bottom of first chamber 33.

Second chamber 41 of combined air barrier and liquid sequencing valve housing 32 as shown in FIGS. 2-5 preferably has an inlet port at its top and an outlet port at its bottom. Second chamber 41 has means associated with its ports that are substantially impervious to air while the set is in use and prevent the flow of air through the secondary flow path. As shown in FIG. 2, the outlet from second chamber 41 is covered by a hydrophilic membrane filter 45.

Hydrophilic membranes 38, 45 are impermeable to air when wet, which they are during the use of the sets of this invention. The hydrophilic filters can be formed from materials such as a cellulose acetate material produced by the Millipore Filter Corporation of Bedford, Mass. or the Sartorius-Membranfilter GmbH of Weender Landstr, West Germany.

The housing 32 of the set shown in FIG. 2 includes an air vent tube 47 having a slide clamp 49 and a filtered opening 50. Alternatively, opening 50 can be filtered by a hydrophobic membrane filter which is permeable by air, but not liquids. The hydrophobic filters can be formed of polyfluorotetraethylene, hexafluoropropylene/tetrafluoroethylene copolymer, or other suitable materials. One such filter is made of Gelman ANH-450 material made by Gelman Instruments of Ann Arbor, Mich. When such a hydrophobic filter is used, slide clamp 49 can be eliminated, as shown in the set of FIG. 5, which includes both a hydrophobic filter over opening 50 and a hydrophilic membrane filter 51 between opening 50 and second chamber 41. Alternatively, the air vent can be eliminated altogether in those instances where the second chamber 41 can be primed through its inlet port.

The sets of FIGS. 2 and 5 each include a slide clamp 51 near the distal end of secondary tube 19 and a slide clamp 52 near the proximal end of common tube 21.

The combined air barrier and liquid sequencing valve shown in FIG. 2 has an aperture in vertical wall 34 near its top which is covered by a hydrophobic membrane 53. Membrane 53 prevents liquid from passing between first and second chambers 33, 41 but permits air to pass. Second chamber 41 has a reservoir 55 for liquid which has an open top located directly under the opening to second chamber 41. Preferably, vertical wall 34 can be an integral part of reservoir 55.

For simplicity, the equipment sets embodying the system of FIG. 1 have been depicted and described as integral units in FIGS. 2 and 5. It is apparent, however, that the sets can be manufactured and assembled in subsets of the entire set and that each subset will accordingly be provided such resealable closures, piercing means, adapters, etc. as are necessary to permit their easy assemblage into the complete set at an appropriate time. It will also be apparent that some of the several components of the sets of FIGS. 2-5 can be interchanged or combined in combinations other than those specifically depicted.

OPERATION OF THE SYSTEM

As depicted in FIGS. 2-5, primary container 11 is suspended in space at a height above the patient by means of a hook 77 and stand 79. It will be apparent that other means for suspending the containers of this invention are well known.

To insure that all the air that might be forced into the patient has been removed from the set, the set is initially primed by first closing all slide clamps 49, 51, and 52, if present. Piercing pin 23 is then inserted into the resealable closure of primary container 11. Primary flow control 31 is fully opened. Slide clamp 52 is opened to allow primary liquid to flow through the primary liquid flow path and force all the air therefrom that might be forced into the patient. Slide clamp 52 is then closed.

In the sets of FIGS. 2 and 5, air will pass through hydrophilic membrane 38 initially until the primary liquid fills first chamber 33 and then wets hydrophilic membrane 38 as it passes through it. Then air will no longer pass through membrane 38.

Secondary flow control 43 and clamp 49 on air vent 47 of second chamber 41 are then opened to allow primary liquid to flow into, or back-prime, secondary flow path 19 until the liquid is above and forces all the air therein above the outlet to second chamber 41, in the set of FIG. 2. Slide clamp 49 is then closed. When the set of FIG. 5 is employed, primary liquid will flow into, or back-prime, secondary flow path 19 until liquid reaches and wets hydrophilic membrane 51, which can then no longer vent air, thereby preventing the further flow of liquid into secondary tube 19. In the sets of FIGS. 2 and 5, liquid will have now wetted hydrophilic membrane 45 and air will not pass through it. A substantial volume of air will remain in second chamber 41.

Optionally, where the proximal end of secondary tube 19 is detachable from y-tube 29, it will be readily apparent that secondary flow control 43 can be fully closed during the priming of primary tube 17 and remain closed during the initial use of the set for the administration of a primary medical liquid. Subsequently, when it is desired to administer a secondary liquid to a patient, piercing pin 35 at the distal end of secondary tube 19 can be inserted into the resealable closure of secondary container 13, the proximal end of secondary tube 19 detached from y-tube 29, slide clamp 51 opened and secondary liquid allowed to flow through secondary tube 19 until it reaches the proximal end thereof. Slide clamp 51 is then closed and the proximal end of secondary tube 19 reattached to y-tube 29.

Common tube 21, which preferably has an adapter at its proximal end open to the flow of liquid therefrom, is next connected to needle 15, which will generally have been already inserted into a vein of the patient. Slide clamp 52 will then be opened to allow primary liquid to flow through the primary liquid flow path to the patient's vein. Primary flow control 31 is then adjusted to a setting that will provide the desired flow rate for a prolonged infusion of primary liquid into the patient, generally 10-150 ml./hr. As is well known in the medical practice, that flow rate can be visually observed by viewing and counting drops passing through the primary drip chamber 25.

Alternatively, when it is desired to administer a secondary liquid to a patient using the sets of FIGS. 2 or 5, piercing pin 35 of secondary tube 19 is inserted into the resealable closure of secondary container 13. If the portion of secondary tube 19 above the inlet port to second chamber 41 is detachable, it can then be detached and slide clamp 51 opened to force the air from that portion of tube 19. Slide clamp 51 is then closed and the tubing attached to the inlet port to second chamber 41.

Secondary container 13 is then suspended in space at a height substantially greater than the height of primary container 11. The set will now be in the mode illustrated in FIG. 2.

When slide clamp 51 is opened, secondary liquid will then immediately begin to flow into reservoir 55 of second chamber 41. Because hydrophilic membrane 45 was wetted during the initial priming of the set and because slide clamp 49 is closed, or hydrophilic membrane 51 is wet, air can only escape from second chamber 41 through the aperture in vertical wall 34 into first chamber 33. Thus, as secondary liquid enters reservoir 55, the air it displaces will be forced through hydrophobic membrane 53 into first chamber 33 by the pressure of the secondary liquid.

Because hydrophilic membrane 38 is wet, air in first chamber 33 cannot pass through it. Therefore, as the pressure of secondary liquid entering reservoir 55 continues to force air through membrane 53 into first chamber 33, that air will accumulate along the top wall of chamber 33. Because the pressure of secondary liquid forcing the air into chamber 33 is greater than the pressure of primary liquid contacting the air, the air displaces the primary liquid in first chamber 33.

The displaced primary liquid is forced away from outlet 36 of first chamber 33 through inlet 30 into primary container 11, as shown in FIG. 3. Thus, hydrophilic membrane 38 and the air displaced from second chamber 41 block the flow of primary liquid from primary container 11 through the primary liquid flow path as long as the height of secondary liquid in the system is greater than that of the primary liquid.

As shown in FIGS. 3 and 5, once reservoir 55 becomes filled with secondary liquid, it will overflow reservoir 55 and flow out of second chamber 41 through its outlet port. Secondary flow control 43 is then adjusted to a desired flow rate, typically 50-250 ml./hr., for the secondary liquid, which will then flow until the liquid in secondary container 13 is depleted. It will be apparent that the initial liquid flowing from secondary tube 19 will be the liquid with which it was primed.

When the height of primary liquid in the system of FIG. 1, as depicted in the sets of FIGS. 2 and 5 becomes greater than the height of the secondary liquid, the valve means associated with the ports of first chamber 33 will immediately open and allow primary liquid to flow from the primary container at the flow rate to which primary flow control 31 is adjusted. Because the pressure of the primary liquid pushing on the air at the top of first chamber 33 is now greater than that of the secondary liquid, the primary liquid forces the air back into second chamber 41, as shown in FIG. 4, thereby unlocking the "air lock" that had prevented primary liquid from flowing out of first chamber 33.

The primary flow rate is independent of the secondary flow rate. In those instances where it is less than or equal to the secondary flow rate, both primary and secondary liquid will flow through common tube 21, until air reaches the air barrier in second chamber 41. Then only primary liquid will enter common tube 21. The air barrier in second chamber 41 then prevents air from being drawn into common tube 21 and eventually to the patient's vein.

When primary container 11 becomes depleted of primary liquid, the primary piercing pin 23 is merely removed therefrom and inserted into the resealable closure of a new primary container, which is then suspended in place of the previous container. When secondary container 13 becomes depleted of secondary liquid, it can be left empty until another secondary liquid is to be administered. When another secondary liquid is to be administered, the secondary piercing pin 35 is merely removed from secondary container 13 and inserted into a new secondary liquid container. The combined air barrier and liquid sequencing valve is then briefly inverted to spill any liquid from reservoir 55 remaining therein and the procedure used for initiating the flow of secondary liquid from the first secondary container is repeated.

Having described the invention in specific detail and exemplified the manner in which it may be carried into practice, it will now be readily apparent to those skilled in the art that innumerable variations, applications, modifications and extensions of the basic principles involved may be made without deparating from its sphere or scope.

I claim:

1. A combined air barrier and liquid sequencing valve providing separate flow paths therethrough for a first and second liquid, preventing the passage of air from said separate flow paths and effecting the automatic interruption of the flow of said first liquid whenever said second liquid is flowing therethrough under a greater pressure than that of said first liquid and the automatic resumption of the flow of said first liquid whenever the flow of said second liquid through said valve ceases, said valve comprising:

a housing divided into first and second chambers by a vertical wall having an aperture therethrough, said aperture covered by a hydrophobic membrane, whereby air can pass between said first and second chamber, said first chamber having an inlet port thereto, and an outlet port at the top thereof covered by a hydrophilic membrane, whereby air is prevented from passing through said outlet, said second chamber having an inlet port thereto, and an outlet port therefrom covered by a hydrophilic membrane, whereby air is prevented from passing from said outlet, and a reservoir for liquid spaced between said inlet and outlet thereto, said reservoir having an open top located directly under said inlet port to said second chamber, whereby, with said primary liquid flowing through said first chamber, said secondary liquid entering said second chamber through said inlet port thereto fills said reservoir until said secondary liquid overflows from said reservoir and flows through said outlet port thereof and air present in said reservoir prior to its displacement therefrom by said secondary liquid escapes from said second chamber through said hyrdophobic membrane covering said aperture in said vertical wall between said first and second chambers under the pressure of said second liquid, thereby forcing said first liquid away from said outlet to said first chamber and interrupting the flow of said first liquid until the flow of said second liquid through said second chamber ceases and allows said first liquid to force said air through said hydrophobic membrane and resume flowing through said first chamber.

2. The combined air barrier and liquid sequencing valve defined in claim 1, wherein said inlet port to said first chamber is at the bottom thereof and said inlet and outlet ports to said second chamber are respectively at the top and bottom thereof.

3. The combined air barrier and liquid sequencing valve defined in claim 1 or 2, wherein said reservoir is integral to said vertical wall between said first and second chambers.

4. The combined air barrier and liquid sequencing valve defined in claim 1, 2 or 3, wherein said second chamber further includes a closable air vent thereto.

5. The combined air barrier and liquid sequencing valve defined in claim 4, wherein said air vent is covered by a hydrophobic membrane.

6. The combined air barrier and liquid sequencing valve of claim 5, wherein said air vent further includes a hydrophilic membrane between said second chamber and said hydrophobic membrane.

* * * * *